(12) United States Patent
Ewart et al.

(10) Patent No.: US 7,691,388 B2
(45) Date of Patent: Apr. 6, 2010

(54) **COMPOSITIONS COMPRISING *PORPHYRA* AND METHODS OF MAKING AND USING THEREOF**

(75) Inventors: Harry Stephen Ewart, Halifax (CA); Junzeng Zhang, Halifax (CA); Colin James Barrow, Halifax (CA)

(73) Assignee: Ocean Nutrition Canada Limited, Dartmouth, NS (CA)

( * ) Notice: Subject to any disclaimer, the term of this patent is extended or adjusted under 35 U.S.C. 154(b) by 0 days.

(21) Appl. No.: 11/388,574

(22) Filed: Mar. 24, 2006

(65) Prior Publication Data

US 2007/0220806 A1    Sep. 27, 2007

(51) Int. Cl.
*A61K 35/80* (2006.01)
(52) U.S. Cl. ............................ 424/195.17
(58) Field of Classification Search ............... None
See application file for complete search history.

(56) References Cited

U.S. PATENT DOCUMENTS

| | | | |
|---|---|---|---|
| 3,195,271 A | 7/1965 | Golueke et al. | 47/1.4 |
| 3,879,890 A | 4/1975 | Chen et al. | 47/1.4 |
| 4,235,043 A | 11/1980 | Harasawa et al. | 47/1.4 |
| 4,981,699 A * | 1/1991 | Inada et al. | 426/7 |
| 5,089,481 A * | 2/1992 | Muto et al. | 514/54 |
| 5,160,736 A * | 11/1992 | Kiriyama | 424/195.17 |
| 5,350,588 A | 9/1994 | Campbell | 426/431 |
| 6,056,476 A | 5/2000 | Streichenberger | 405/24 |
| 6,199,317 B1 | 3/2001 | Saiki et al. | 47/1.4 |
| 6,217,879 B1 * | 4/2001 | Suetsuna et al. | 424/195.17 |
| 6,579,714 B1 | 6/2003 | Hirabayashi et al. | 435/292.1 |
| 6,698,134 B1 | 3/2004 | Li et al. | 47/1.4 |
| 6,986,323 B2 * | 1/2006 | Ayers | 119/200 |
| 2004/0047895 A1 * | 3/2004 | Hagino et al. | 424/439 |
| 2004/0131636 A1 * | 7/2004 | Hagino et al. | 424/195.17 |
| 2004/0228875 A1 | 11/2004 | Laclerc et al. | |
| 2005/0120624 A1 * | 6/2005 | Levy | 47/59 R |

FOREIGN PATENT DOCUMENTS

| | | |
|---|---|---|
| EP | 0462020 | 6/1991 |
| EP | 0 438 302 | 7/1991 |
| EP | 1 433 500 | 6/2004 |
| JP | 57169422 A * | 10/1982 |
| JP | 62100294 A * | 5/1987 |
| JP | 62294068 A * | 12/1987 |
| JP | 03284626 * | 12/1991 |
| JP | 03284626 A * | 12/1991 |
| JP | 04210535 | 7/1992 |
| JP | 2004049072 A * | 2/1994 |
| JP | 06217657 | 8/1994 |
| JP | 07008213 * | 1/1995 |
| JP | 07008213 A * | 1/1995 |
| JP | 11113434 | 4/1999 |
| JP | 2002065223 A * | 3/2002 |
| JP | 2002238384 | 8/2002 |
| JP | 2004/339161 | 12/2004 |
| JP | 2005/270024 | 10/2005 |
| WO | WO 94/24984 | 11/1994 |
| WO | WO 99/29160 | 6/1999 |
| WO | WO 99/39718 | 8/1999 |
| WO | WO 2005/051073 | 6/2005 |

OTHER PUBLICATIONS

Bidlingmeyer et al., "Rapid analysis of amino acids using pre-column derivatization," *J. Chromatography*, 336:93-104, 1984.
Cohen and Strydon, "Amino acid analysis utilizing phenylisothiocyanate derivatives," *Anal. Biochem.*, 174:1-16, 1988.
Heinrikson and Meredith, "Amino acid analysis by reverse phase HPLC: pre-column derivatization with phenylisothiocyanate," *Anal. Biochem.*, 136:65-74, 1984.
Huang et al., "High-throughput assay of oxygen radical absorbance capacity (ORAC) using a multichannel liquid handling system coupled with a microplate fluorescence reader in 96-well format," *J. Apr. Food Chem.*, 50:4437-44, 2002.
Li et al., "Phytoplankton pigment analysis by HPLC and its applications in algal community investigations," *Bot. Bull. Acad. Sin.*, 43:283-90, 2002.
Lubchenco and Cubit, "The heteromorphic life histories of certain marine algae as adaptations to variations in herbivory," *Ecology*, 61(3):676-687, 1980.
Pessin and Bell, "Mammalian facilitative glucose transporter family: structure and molecular regulation," *Annu. Rev. Physiol.*, 54:911-930, 1992.
Reyes and Subryan, "An improved method of simultaneous HPLC and thiamin in selected cereal products," *J. Food Composition & Anal.*, 2(1):41-47, 1989.
Waaland et al., "Conchocelis growth and photoperiodic control of conchospore release in *Porphyra torta*," *J. Phycology*, 23:406-14, 1987.
Zhang et al., "Analytical approach to the discoloration of edible laver 'Nori' in the Ariake Sea," *Anal. Sci.*, 20:37-43, 2004.
Lee et al., "Preparation of noodle with laver powder and its characteristics," *Korean J Food Sci Tech* 32(2):298-305 (2000) (ABSTRACT).
Invitation to Pay Additional Fees for PCT/IB2007/002849 mailed Jul. 23, 2008.

* cited by examiner

*Primary Examiner*—Christopher R. Tate
(74) *Attorney, Agent, or Firm*—Ballard Spahr LLP

(57) ABSTRACT

Disclosed herein are compositions comprising *Porphyra*, as well as methods of making and using such compositions.

25 Claims, 5 Drawing Sheets

A. Injection (i.p.)

B. Oral (gavage)

FIGURE 5

COMPOSITIONS COMPRISING *PORPHYRA* AND METHODS OF MAKING AND USING THEREOF

FIELD

The disclosed subject matter generally relates to compositions comprising *Porphyra*, as well as to methods of making and using such compositions.

BACKGROUND

The red marine alga *Porphyra* is high in protein, vitamins, minerals, and soluble fiber, and it is the most widely eaten and commercially valuable seaweed in the world. Commonly called "Nori," it is commercially grown in the open seas off the coasts of Japan, China, Korea, and Taiwan on nets covering nearly 70,000 hectacres. Annual harvests result in over 130,000 metric tons, with sales totaling over $6 billion US dollars. The market for Nori sheets in the US alone is estimated to be worth at least $50 million dollars annually and is growing at a rate of over 17% per year.

The development of cultivation techniques to reduce costs, increase yield, and to enhance the levels of various nutrients in Nori has been of major importance. Some improvements made to the technical aspects of Nori cultivation include the development of techniques for controlled culturing using land-based seawater ponds and for artificial seeding of spores onto cultivation nets, which can be stored until placed in the ocean.

With approximately 70 species of *Porphyra* worldwide, genetic improvement of cultured species has also been crucial for maximizing yield and developing cost-effective cultivation programs. To this end, classical breeding methods, particularly strain selection, have been the most successful at improving seaweed cultivation techniques. For example, as a result of strain selection efforts, there are several dozen cultivars of two *Porphyra* species, *P. yezoensis* and *P. tenera*, farmed in Japan. These cultivars were developed primarily as a result of an intensive strain selection program in Japan. Over many years of repeated selection, improvements were made in increasing the average length of fronds, as well as the length of the growing seasons of these two species.

Despite the success of such efforts to improve cultivation techniques, there are still a number of challenges, disadvantages, and limitations. In particular, repeated strain selection usually requires many years of intensive effort and is very labor intensive. Thus, selecting particular strains of *Porphyra* that yield desired levels of various nutrients can be difficult. In addition, the existing genetic variability in one or more populations of interest may not be sufficient for strain selection purposes. This can limit strain selection techniques to those varieties with high genetic variability, potentially foreclosing the use of strains that may contain desirable nutrient levels but that may not have the genetic variability suitable for strain selection.

What are needed are methods that allow one to obtain multiple types of *Porphyra* compositions without the need to cultivate multiple strains of *Porphyra*. Also needed are methods that can be used to produce specific and tailored *Porphyra* compositions but that minimize the use of specialized cultivation or strain selection techniques. Compositions prepared from such methods, and methods of using such compositions are also needed. Disclosed herein are compositions and methods that meet these and other needs.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In another aspect, the disclosed subject matter relates to compositions comprising *Porphyra*, and to nutritional supplements, foodstuffs, and pharmaceutical compositions comprising such compositions. In still another aspect, the disclosed subject matter relates to methods of preparing such *Porphyra* containing compositions. Still further, the disclosed subject matter relates to delivery devices containing such compositions and to methods of preparing the delivery devices. In yet another aspect, the disclosed subject matter relates to methods of using the described compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying Figures, which are incorporated in and constitute a part of this specification, illustrate several aspects described below.

DETAILED DESCRIPTION

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an extract" includes mixtures of two or more such extracts, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data is provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

Reference will now be made in detail to specific aspects of the disclosed materials, compounds, compositions, articles, and methods, examples of which are illustrated in the accompanying Examples and Figures.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components or residues A, B, and C are disclosed as well as a class of components or residues D, E, and F, and an example of a combination compound A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Ocean Nutrition Canada (Dartmouth, NS, Canada); Noritech Seaweed Biotechnologies Ltd (Yokneam; Israel), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

In one aspect, disclosed herein are compositions comprising *Porphyra*. For example, disclosed herein are compositions comprising a blend of *Porphyra* and an extract of *Porphyra*. In other examples, disclosed herein are compositions comprising an extract of *Porphyra*. By the term "*Porphyra*" is meant any member (e.g., species, subspecies, varieties, forms) belonging to the *Porphyra* genus of marine alga, including selected and genetically modified strains, regardless of origin or place of cultivation, particular stage during the life cycle (e.g., spermatia, carpospores, conchocells, conchospore, aplanospore, thalus, plantlets, and the like), or whether it has been processed or unprocessed. Further, the term "*Porphyra*" is used interchangeably herein with the word "Nori." Other commercial names for *Porphyra* are Amanori, Ana-amanori, Asakusa nori, Beni-tasa, California layer, Casóg, Chi Choy, Chi Tsai, and Chishima Kuro-nori. By preparing blends of *Porphyra* and an extract of *Porphyra*, one can arrive at compositions with specifically designed nutrient/component profiles that are not obtainable by strain selection or cultivation techniques alone. Further, the disclosed methods can be used to provide compositions with consistent nutrient/component profiles, thereby reducing the variability seen with *Porphyra* based compositions prepared by other methods.

*Porphyra*

In some examples disclosed herein, the *Porphyra* is *P. abbotae, P. acanthophora, P. atropurpurae, P. columbina, P. crispata, P. fallax, P. leucostica, P. perforata, P. pseudolanceolata, P. spirilis, P. suborticulata, P. torta, P. umbilicalis,* or *P. vietnamensis*, including mixtures thereof. Other examples include, but are not limited to, *P. tenera, P. haitanensis, P. pseudolinearis, P. kuniedae, P. arasaki, P. purpurea,* and *P. seriata*, including mixtures thereof. The *Porphyra* species and variants disclosed in WO 99/29160 can also be used in the methods and compositions disclosed herein. In some specific examples, the *Porphyra* is *P. yezoensis, P.* sp. *Taiwanese,* or mixtures thereof.

The *Porphyra* disclosed herein can be obtained from commercial sources, or can be cultivated and harvested by methods disclosed in, for example, Bold and Wynne, Introduction to the Algae: Structure and Reproduction, Prentice-Hall, Inc., 1978; Lobban and Wynne, "The Biology of Seaweeds," University of California Press, 1981; Lubchenco and Cubit, "The heteromorphic life histories of certain marine algae as adaptations to variations in herbivory," Ecology 61(3):676-687, 1980; Waaland et al., "Conchocelis growth and photoperiodic control of conchospore release in *Porphyra torta*," J. Phycology. 23:406-414, 1987; U.S. Pat. Nos. 3,195,271, 6,056,476, and Publication No. WO 99/29160, which are incorporated by reference herein at least for their teachings of *Porphyra* and methods for its cultivation.

In some specific examples, *Porphyra* that can be used in the compositions and methods disclosed herein can be obtained by methods disclosed in Publication No. WO 05/051073 to NoriTech Seaweed Biotechnologies (Yoqneam, Israel), which is incorporated by reference herein for its teachings of specific *Porphyra* species and methods for their cultivation. For example, *Porphyra* can be prepared in a system for land based cultivation of seaweeds that comprises laboratory facilities suitable to produce spores and sporlings in cultures, a plurality of sleeves to allow the maturation of the sporlings, a plurality of small inoculation tanks containing seawater enriched with nutrients under optimal conditions to allow the mature sporlings to grow into seaweed pieces, and a plurality of large cultivation tanks to allow the seaweed pieces to grow into full size. In another specific example, *Porphyra* suitable for use in the disclosed compositions and methods can be prepared by producing spores and sporlings in cultures maintained in a laboratory facility, growing the sporlings in suspension cultures under optimal growth conditions, transferring the matured sporlings to large cultivation tanks to allow for rapid growth, harvesting the full grown seaweed pieces, drying and grinding the harvested seaweeds, and preparing the resulting seaweed for human consumption.

Also, the following seaweeds can be use in the disclosed methods either in the place of or in addition to *Porphyra: Laminaria, Undaria, Eucheuma, Gracilaria, Ulva, Sargassum, Codium, Cladophora, Ascophyllum, Palmaria, Furcellaria, Fucus, Enteromorpha, Nemacystus, Kjellmaniella, Hizikia, Gelidium, Gloiopeltis, Hemineura, Spirogyra,* and *Acetabularia,* including mixtures thereof.

Extract of *Porphyra*

The extract of *Porphyra* can be obtained from any *Porphyra* disclosed herein. In particular, this extract can be obtained by aqueous and/or organic extractions of *Porphyra*. Suitable extraction solvents that can be used include, but are not limited to, water, acidic aqueous solutions (e.g., solutions of HCl, $H_2SO_4$, $H_3PO_4$, $HNO_3$, or acetic acid), basic aqueous solutions (e.g., solutions of KOH, NaOH, $Na_2CO_3$, $K_2CO_3$, $NaHCO_3$ and the like), methanol, ethanol, propanol, isopropanol, hexane, and mixtures thereof, such as methanol:water, and ethanol:water. In specific examples, the *Porphyra* extract can be obtained by contacting *Porphyra* with the extraction solvent, e.g., water, an aqueous solvent, or an organic solvent. The resulting mixture can optionally be heated and/or stirred. Generally, higher temperatures and/or stirring can improve the efficiency of the extraction. Typically, when the extraction solvent is water or an aqueous solution, the mixture can be heated to at least about 80° C., 70° C., 60° C., 50° C., 40° C., 30° C., or 20° C., where any of the stated values can form an upper or lower endpoint when appropriate. In particular examples, the extraction can be conducted at from about 60 to about 95° C. When organic solvents are used as the extraction solvent, the mixture can be heated to temperatures below the boiling point of the organic extraction solvent. Stirring the mixture can be accomplished by any method known in the art, e.g., a mechanical stirrer, a magnetic stir bar, shaking, sonication, bubbling gas through the mixture, and the like.

The mixture of *Porphyra* and extraction solvent can be separated by various methods. For example, filtration (e.g., filter paper, frits, gel filtration, and ultrafiltration), chromatography, reverse osmosis, dialysis, or centrifugation can be used to separate the extraction solvent from the extracted *Porphyra* residue. It is contemplated herein that the extracted *Porphyra* residue can be subjected to one or more additional extractions as described above. It is also contemplated that any subsequent extractions can be the same or different from those described above. For example, while a first extraction can use an aqueous extraction solvent at higher temperatures, a subsequent extraction can use an organic solvent at lower temperatures, and vice-versa. The particular extraction solvents and the number and type of extractions will depend on the preference of the researcher, costs, the particular nutrients that are desired to be obtained, and the like.

In one example, a Nori extract can be obtained by one or more water extractions of Nori, where the various extracts can be combined and optionally dried. In other examples, a Nori extract can be obtained by first extracting Nori (e.g., Nori powder from Noritech Seaweed Biotechnologies Ltd (Yokneam; Israel)) with hexane. The remaining residue can be extracted again with ethanol (95%). The residue from this extraction can then be extracted with water at room temperature. The residue from the room-temperature-water extraction can then be extracted with water at elevated temperatures (e.g., about 80° C.).

In certain examples disclosed herein, the extracts obtained from each extraction of *Porphyra* can combined and then dried by methods such as spray drying, lyophilization, evaporation, and the like.

Compositions

Various compositions disclosed herein comprise *Porphyra*, as disclosed above, and an extract of *Porphyra*, also disclosed above. The disclosed compositions can be prepared by blending the *Porphyra* with the extract of *Porphyra*. Blending can be accomplished by mixing the liquidous extraction solvent or the dried extract with the *Porphyra*. In some examples, the *Porphyra* can be dried-milled. Blending the *Porphyra* and the *Porphyra* extract can further involve grinding and/or milling to produce a fine powder.

The ratio of *Porphyra* to extract of *Porphyra* in the disclosed compositions can be about 1:10 to 10:1 parts by weight. Specific examples include compositions that contain about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1 parts by weight *Porphyra* to extract of *Porphyra*. Still other examples include compositions that contain from about 1 to about 10, from about 2 to about 8, or from about 4 to about 6 parts by weight of *Porphyra* to from about 1 to about 10, from about 2 to about 8, or from about 4 to about 6 parts by weight of extract of *Porphyra*. In one particular example, the compositions can contain about 1:1 parts by weight of *Porphyra* to extract of *Porphyra*.

In the disclosed compositions, the *Porphyra* and the extract of *Porphyra* can be obtained from the same species, strain, or variant of *Porphyra*. For example, the *Porphyra* species, strain, or variant that is extracted, as disclosed herein, can be the same as the *Porphyra* that is combined with the extract to produce a composition as disclosed herein. In other examples, the *Porphyra* and the extract of *Porphyra* blended therewith can be from one or more different species, strains, or variants of *Porphyra*. Using different *Porphyra* species, strains, and/or variant in this way can allow one to prepare compositions that have the characteristics (e.g., nutrient levels) of each of the different *Porphyra* sources. Thus, one can tailor compositions so that they contain desired levels of nutrients. For example, one can blend an extract from one *Porphyra* species that is rich in certain nutrients with another *Porphyra* species that rich in other nutrients, obtaining a composition that contains the nutrients from both *Porphyra* species.

The disclosed *Porphyra* compositions can be a free flowing purple powder, with salty and savory smell and taste. In general, the moisture content of the disclosed compositions can be less than about 6%, less than about 5%, or less than about 4%. In a particular example, the disclosed composition can have a moisture content of about 4.5%. Moisture content can be determined as described in the Official Methods of Analysis of AOAC INTERNATIONAL, 15$^{th}$ Edition, 1990, 950.46, p. 931, which is incorporated by reference herein for its teachings of analytical methods related to moisture content.

The residue on ignition (Ash) of the disclosed compositions can be less than about 40%, less than about 35%, less than about 30%, or less than about 25%, based on the total weight of the composition. In a particular example, the disclosed composition can have a residue on ignition (Ash) of about 29%. Ash content can be determined as described in the Official Methods of Analysis of AOAC INTERNATIONAL, 15$^{th}$ Edition, 1990, 920.155c, p. 947, which is incorporated by reference herein for its teachings of analytical methods related to ash content.

The total dietary fiber of the disclosed compositions can be greater than about 25%, greater than about 30%, greater than about 35%, or greater than about 40%, based on the total weight of the composition. In a particular example, the disclosed composition can have about 35% total dietary fiber. Dietary fiber content can be determined as described in the Official Methods of Analysis of AOAC INTERNATIONAL, 15$^{th}$ Edition, 1990, 993.19/991.42, which is incorporated by reference herein for its teachings of analytical methods related to dietary fiber content.

The total lipids of the disclosed compositions can be greater than about 0.5%, greater than about 1.0%, greater than about 1.5%, or greater than about 2.0%. In a particular example, the disclosed composition can have about 1.8% total lipids. Total lipid content can be determined as described in the Official Methods of Analysis of AOAC INTERNATIONAL, 15$^{th}$ Edition, 1990, 963.15 (soxhlet), which is incorporated by reference herein for its teachings of analytical methods related to total lipid content.

The disclosed compositions can contain several pigments. For example, the disclosed compositions can contain from about 7.0 to about 11.0, from about 8.0 to about 10.0, or about 9.0 (e.g., 9.11) mg/g of phycoerythrin. In another example, the disclosed compositions can contain from about 3.0 to about 6.0, from about 4.0 to about 5.0, or about 4.5 (e.g., 4.63) mg/g of phycocyanin. In yet another example, the disclosed compositions can contain from about 0.1 to about 0.5, from about 0.15 to about 0.35, or about 0.25 (e.g., 0.29) mg/g of chlorophyll a. In still another example, the disclosed compositions can contain from about 0.001 to about 0.100, from about 0.050 to about 0.075, or about 0.060 (e.g., 0.054) mg/g of lutein. In a further example, the disclosed compositions can contain from about 0.010 to about 0.050, from about 0.015 to about 0.035, or about 0.025 (e.g., 0.027) mg/g of beta-carotene. Methods of determining amounts of phycoerythrin and phycocyanin are described in Zhang et al., "Analytical approach to the discoloration of edible layer 'Nori' in the Ariake Sea," *Anal. Sci.*, 20:37-43, 2004. Methods of determining amounts of chlorophyll a, lutein, and beta-carotene are described in Li et al., "Phytoplankton pigment analysis by HPLC and its applications in algal community investigations," *Bot. Bull. Acad. Sin.*, 43:283-290, 2002. These references are incorporated by reference herein for their teachings of pigment analysis.

Also, the disclosed compositions can have antioxidant activity (i.e., Oxygen Radical Absorbance Capacity (ORAC) assay) of from about 40 to about 60, from about 45 to about 55, or about 50 (e.g., 53) μmole TE/g. Methods of determining antioxidant activity (ORAC) are described in Huang et al., "High-throughput assay of oxygen radical absorbance capacity (ORAC) using a multichannel liquid handling system coupled with a microplate fluorescence reader in 96-well format," *J. Agr. Food Chem.*, 50:4437-4444, 2002, which is incorporated by reference herein for its teachings of methods for determining antioxidant activity.

The disclosed compositions can also contain various amino acids and proteins. For example, the total protein content of the disclosed compositions can be from about 25 to about 50, from about 30 to about 40, or about 35% (e.g., 32.5%), based on the total weight of the composition. Total protein content can be determined as described in the Official Methods of Analysis of AOAC INTERNATIONAL, 15$^{th}$ Edition, 1990, 981.10, p. 973, which is incorporated by reference herein for its teachings of analytical methods related to determining protein content.

In other examples, the total essential amino acid content of the disclosed compositions can be from about 7.0 to about 10, from about 8 to about 9, or about 8.5% (e.g., 8.3%), based on the total weight of the composition. In still other examples, the disclosed compositions can have from about 10 to about 30, from about 15 to about 25, or about 20% (e.g., 22.02%) total conditionally essential or non-essential amino acids, based on the total weight of the composition.

Specific amino acids that can be present in the disclosed compositions include, but are not limited to, isoleucine, which can be present in an amount of at least about 6, at least about 7, at least about 8, or at least about 9 mg/g (e.g., about 8.91 mg/g); leucine, which can be present in an amount of at least about 14, at least about 16, at least about 17, or at least about 18 mg/g (e.g., about 17.20 mg/g); lysine, which can be present in an amount of at least about 10, at least about 11, at least about 12, or at least about 13 mg/g (e.g., about 12.61 mg/g); methionine, which can be present in an amount of at least about 2, at least about 3, at least about 4, or at least about 5 mg/g (e.g., about 4.30 mg/g); phenylalanine, which can be present in an amount of at least about 6, at least about 7, at least about 8, or at least about 9 mg/g (e.g., about 8.73 mg/g); threonine, which can be present in an amount of at least about 10, at least about 12, at least about 14, or at least about 16 mg/g (e.g., about 14.62 mg/g); tryptophan, which can be present in an amount of at least about 0.1, at least about 1, at least about 1.5, or at least about 2.0 mg/g (e.g., about 1.67 mg/g); valine, which can be present in an amount of at least about 10, at least about 12, at least about 14, or at least about 16 mg/g (e.g., about 14.95 mg/g); alanine, which can be present in an amount of at least about 25, at least about 30, at least about 35, or at least about 40 mg/g (e.g., about 36.09 mg/g); arginine, which can be present in an amount of at least about 20, at least about 25, at least about 30, or at least about 35 mg/g (e.g., about 30.39 mg/g); aspartic acid, which can be present in an amount of at least about 15, at least about 20, at least about 25, or at least about 30 mg/g (e.g., about 25.41 mg/g); cystine, which can be present in an amount of at least about 5, at least about 6, at least about 7, or at least about 8 mg/g (e.g., about 7.20 mg/g); glutamic acid, which can be present in an amount of at least about 25, at least about 30, at least about 35, or at least about 40 mg/g (e.g., about 37.94 mg/g); glycine, which can be present in an amount of at least about 12, at least about 15, at least about 17, or at least about 20 mg/g (e.g., about 17.46 mg/g); histidine, which can be present in an amount of at least about 1, at least about 2, at least about 3, or at least about 4 mg/g (e.g., about 3.39 mg/g); proline, which can be present in an amount of at least about 7, at least about 9, at least about 11, or at least about 13 mg/g (e.g., about 11.26 mg/g); tyrosine, which can be present in an amount of at least about 5, at least about 6, at least about 7, or at least about 8 mg/g (e.g., about 7.04 mg/g); or taurine, which can be present in an amount of at least about 9, at least about 10, at least about 11, or at least about 12 mg/g (e.g., about 11.49 mg/g). Methods of determining amino acid content are described in Bidlingmeyer et al., "Rapid analysis of amino acids using pre-column derivatization," *J. Chromatography* 336:93-104, 1984; Heinrikson and Meredith, "Amino acid analysis by reverse phase HPLC: pre-column derivatization with phenylisothiocyanate," *Anal. Biochem.* 136:65-74, 1984; and Cohen and Strydom, "Amino acid analysis utilizing phenylisothiocyanate derivatives," *Anal. Biochem.* 174:1-16, 1988, which are all incorporated by reference herein for their teachings of methods for determining amino acid content.

Specific vitamins that can be present in the disclosed compositions include, but are not limited to, vitamin C, which can be present in an amount of at least about 0.1, at least about 0.2, at least about 0.3, or at least about 0.4 mg/g (e.g., about 0.39 mg/g); B1 (Thiamin), which can be present in an amount of at least about 15, at least about 17, at least about 19, or at least about 21 µg/g (e.g., about 19.04 µg/g); B2 (Riboflavin), which can be present in an amount of at least about 35, at least about 40, at least about 45, or at least about 50 µg/g (e.g., 46.02 µg/g); B3 (Niacin), which can be present in an amount of at least about 115, at least about 130, at least about 145, or at least about 160 µg/g (e.g., 141.24 µg/g); B6 (Pyridoxine), which can be present in an amount of at least about 9, at least about 10, at least about 11, or at least about 12 µg/g (e.g., 11.11 µg/g); or folic acid, which can be present in an amount of at least about 7, at least about 8, at least about 9, or at least about 10 µg/g (e.g., 9.20 µg/g).

Methods for determining vitamin C content are described in the Official Methods of Analysis of AOAC INTERNATIONAL, 17$^{th}$ Edition, 2000, 967.22. Methods for determining Vitamin B1 content are described in the Official Methods of Analysis of AOAC INTERNATIONAL, 17$^{th}$ Edition, 2000, 942.23 and 986.27, as well as in Reyes and Subryan, "An improved method of simultaneous HPLC and thiamin in selected cereal products," *J. Food Composition & Anal.*, 2(1): 41-47, 1989. Methods for determining Vitamin B2 content are described in the Official Methods of Analysis of AOAC INTERNATIONAL, 17$^{th}$ Edition, 2000, 970.65, 981.15, and 985.31, as well as in Reyes and Subryan, "An improved method of simultaneous HPLC and thiamin in selected cereal products," *J. Food Composition & Anal.*, 2(1):41-47, 1989. Methods for determining Vitamin B3 content are described in the Official Methods of Analysis of AOAC INTERNATIONAL, 17$^{th}$ Edition, 2000, 960.46, 944.13, and 985.34, as well as in USFDA, "Methods for Microbiological Analysis of Selected Nutrients," AOAC, 1996. These references are all incorporated by reference herein for their teachings of vitamin analysis.

Specific minerals that can be present in the disclosed compositions include, but are not limited to, calcium, which can be present in an amount of at least about 1, at least about 2, at least about 3, or at least about 4 mg/g (e.g., 3.48 mg/g); potassium, which can be present in an amount of at least about 50, at least about 55, at least about 60, or at least about 65 mg/g (e.g., 62.1 mg/g); magnesium, which can be present in an amount of at least about 4, at least about 5, at least about 6, or at least about 7 mg/g (e.g., 6.3 mg/g); manganese, which can be present in an amount of at least about 0.0075, at least about 0.010, at least about 0.025, or at least about 0.050 mg/g (e.g., 0.026 mg/g); sodium, which can be present in an amount of at least about 6, at least about 8, at least about 10, or at least about 12 mg/g (e.g., 10 mg/g); phosphorous, which can be present in an amount of at least about 6, at least about 7, at least about 8, or at least about 9 mg/g (e.g., 8.45 mg/g); or zinc, which can be present in an amount of at least about 0.0075, at least about 0.01, at least about 0.025, or at least about 0.05 mg/g (e.g., 0.033 mg/g).

The disclosed compositions can have low levels of heavy metals, many of which adversely affect health when present in higher levels. For example, the disclosed compositions can have less than about 7, less than about 6, less than about 5, or less than about 4 ppm (e.g., 5.6 ppm) arsenic, less than about 0.75, less than about 0.5, less than about 0.25, or less than about 0.1 ppm (e.g., 0.2 ppm) cadmium, less than about 3, less than about 2, less than about 1, or less than about 0.5 ppm (e.g., 1.7 ppm) lead, or less than about 0.1, less than about 0.05, less than about 0.01, or less than about 0.005 ppm (e.g., <0.01 ppm) mercury.

Supplements

The disclosed compositions can be particularly useful as nutritional supplements. Thus, disclosed herein are nutritional supplements comprising the compositions disclosed herein. A nutritional supplement is any composition that can be administered to or taken by a subject to provide, supply, or increase a nutrient(s) (e.g., vitamin, mineral, essential trace element, amino acid, peptide, nucleic acid, oligonucleotide, lipid, cholesterol, steroid, carbohydrate, and the like).

The nutritional supplement can comprise any amount of the compositions disclosed herein, but will typically contain an amount determined to supply a subject with a desired dose of a particular nutrient found in the disclosed compositions. The exact amount of the disclosed compositions required in the nutritional supplement will vary from subject to subject, depending on the species, age, weight and general condition of the subject, the severity of the dietary deficiency being treated, the particular mode of administration, and the like. Thus, it is not possible to specify an exact amount for every nutritional supplement. However, an appropriate amount can be determined by one of ordinary skill in the art using only routine experimentation given the teachings herein.

The nutritional supplement can also comprise other nutrient(s) that are added int addition to the disclosed *Porphyra* compositions, such as vitamins, minerals, proteins, amino acids, other trace elements, and the like. Further, the nutritional supplement can comprise other components such as preservatives, antimicrobials, anti-oxidants, chelating agents, thickeners, flavorings, diluents, emulsifiers, dispersing aids, or binders.

The nutritional supplements are generally taken orally and can be in any form suitable for oral administration. For example, a nutritional supplement can typically be in a tablet, gel-cap, capsule, liquid, sachets, or syrup form.

Pharmaceutical Formulation

Also, disclosed herein are pharmaceutical formulations. In one aspect, a pharmaceutical formulation can comprise any of the compositions disclosed herein with a pharmaceutically acceptable carrier. For example, a pharmaceutical formulation can comprise a compositions comprising a blend of *Porphyra* and a dried aqueous extract of *Porphyra* and a pharmaceutically acceptable carrier. The disclosed pharmaceutical formulations can be used therapeutically or prophylactically.

By "pharmaceutically acceptable" is meant a material that is not biologically or otherwise undesirable, i.e., the material can be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, 21$^{st}$ ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compositions can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

Foodstuffs

Also disclosed herein are foodstuffs comprising any of the compositions disclosed herein. By "foodstuff" is meant any article that can be consumed (e.g., eaten, drank, or ingested) by a subject. In one aspect, the disclosed compositions can be used as nutritional supplements in a foodstuff. For example, the disclosed compositions can be loaded with compounds that provide health benefits, and they can thus be incorporated into various foodstuffs. In some other examples, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or companion pet food. In other examples, the foodstuff is bread, tortillas, cereal, sausage, chicken, ice cream, yogurt, milk, salad dressing, rice bran, fruit juice, a dry beverage powder, rolls, cookies, crackers, fruit pies, or cakes. Also, the disclosed compositions can be provided in a sachet (e.g., teabag).

Methods of Use

The disclosed compositions have many uses. For example, the disclosed compositions can have antiviral activity, antibacterial activity, antimycobacterial activity, antihelminthic activity, antiulcer activity, anti-inflammatory activity, endocrine effects, metal chelating properties, wound and burn healing properties, antiaging properties, antioxidant properties, anti-atherosclerotic properties, immunomodulatory properties, and offer protection from UV radiation. Particular uses for the disclosed compositions are as anti-diabetic agents.

In one particular example, disclosed herein are methods of supplementing nutrients in a subject by administering an effective amount of a composition comprising a *Porphyra* composition as disclosed herein. In still another example, disclosed herein are methods of improving insulin sensitivity in a subject by administering an effective amount of a *Porphyra* composition as disclosed herein. In a further example, disclosed herein are methods of reducing hyperglycemia in a subject by administering an effective amount of a *Porphyra* composition as disclosed herein. In yet another example, disclosed herein are methods of modulating an immune response in a subject by administering an effective amount of a composition comprising a *Porphyra* composition as disclosed herein. In still another example, disclosed herein are methods of modulating spleen cell proliferation in a subject by administering an effective amount of a composition comprising a *Porphyra* composition as disclosed herein. In still another example, disclosed herein are methods of inhibiting viral infection in a subject by administering an effective amount of a composition comprising a *Porphyra* composition as disclosed herein.

It is contemplated that the methods disclosed herein can be accomplished by administering various forms of the disclosed compositions. For example, one can administer any of the pharmaceutical formulations with any of the foodstuffs disclosed herein. In another example, one can administer a tablet or capsule with any of the nutritional supplements disclosed herein. In yet another example, one can administer any of the pharmaceutical formulations with any of the delivery devices and nutritional supplement disclosed herein, and the like.

Dosage and Delivery

When used in the above described methods or other treatments, or in the nutritional supplements, pharmaceutical formulations, or foodstuffs disclosed-herein, an "effective amount" of one of the disclosed compositions can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of the composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in the event of any counter-indications. Dosage can vary, and can be administered in one or more dose administrations daily, for one or several days. Guidance can be found in the literature for appropriate dosages for given classes of pharmaceutical products.

Further, disclosed are methods for delivering a disclosed composition to a subject by administering to the subject any of the nutritional supplements, pharmaceutical formulations, delivery devices, and/or foodstuffs disclosed herein. The disclosed compositions (including nutritional supplements, delivery devices, and pharmaceutical formulations) can typically be administered orally.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention that are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

*Porphyra* Composition

Figure 1:
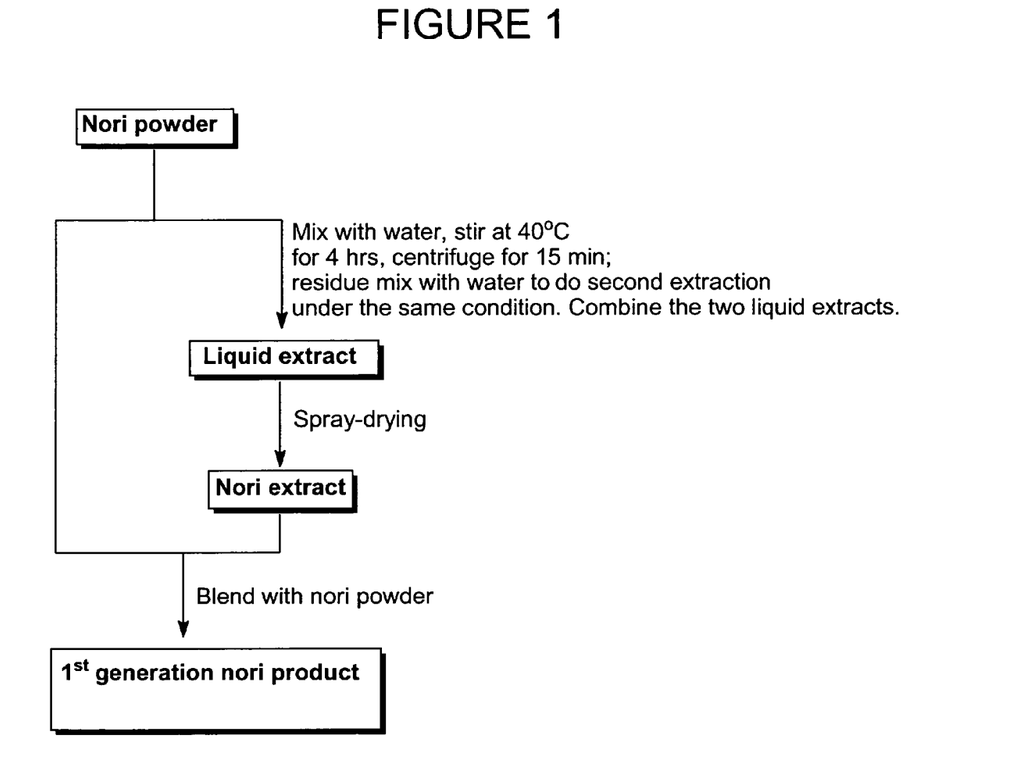
FIG. 1 is a schematic showing a blending procedure for the production of compositions as disclosed herein.

A *Porphyra* composition, as disclosed herein, was prepared by blending dried-milled Nori and a Nori extract as shown in FIG. 1. In brief, Nori seaweed obtained from Noritech Seaweed Biotechnologies Ltd (Yokneam; Israel) washed to remove adherent salt, dried, and grounded to a fine powder (called "dried-milled Nori").

The dried-milled Nori powder was then mixed with water, stirred at 40° C. for 4 hours, and centrifuged for 15 minutes. The aqueous phase was collected. The remaining residue was again mixed with water for a second extraction under the same conditions as before. The aqueous phase from this second extraction was combined with the aqueous phase from the first extraction. After spray drying the combined aqueous phases, the resulting dried Nori extract was then blended with additional dried-milled Nori powder. The characteristics of this *Porphyra* composition are provided in Table 1.

TABLE 1

*Porphyra* composition

Appearance/Organoleptic: Free flow purple powder, with salty and savory smell and taste.

| | |
|---|---|
| Moisture | 4.5% |
| Residue on Ignition (Ash) | 29% |
| Total Dietary fiber | 35% |
| Total lipids | 1.8% |
| Pigments | |
| Phycoerythrin | 9.11 mg/g |
| Phycocyanin | 4.63 mg/g |
| Chlorophyll a | 0.29 mg/g |
| Lutein | 0.054 mg/g |
| Beta-carotene | 0.027 mg/g |
| Antioxidant activity (ORAC) | 53 μmole TE/g |
| Proteins and Amino Acids | |
| Protein | 32.5% |
| Total essential amino acids | 8.30% |
| Isoleucine | 8.91 mg/g |
| Leucine | 17.20 mg/g |
| Lysine | 12.61 mg/g |
| Methionine | 4.30 mg/g |
| Phenylalanine | 8.73 mg/g |
| Threonine | 14.62 mg/g |
| Tryptophan | 1.67 mg/g |
| Valine | 14.95 mg/g |
| Total conditionally essential or non-essential amino acids | 22.02% |
| Alanine | 36.09 mg/g |
| Arginine | 30.39 mg/g |
| Aspartic acid | 25.41 mg/g |
| Cystine | 7.20 mg/g |
| Glutamic acid | 37.94 mg/g |
| Glycine | 17.46 mg/g |
| Histidine | 3.39 mg/g |
| Proline | 11.26 mg/g |
| Tyrosine | 7.04 mg/g |
| Taurine | 11.49 mg/g |
| Vitamins | |
| Vitamin C | 0.39 mg/g |
| B1 (Thiamin) | 19.04 μg/g |
| B2 (Riboflavin) | 46.02 μg/g |
| B3 (Niacin) | 141.24 μg/g |
| B6 (Pyridoxine) | 11.11 μg/g |
| Folic Acid | 9.20 μg/g |
| Minerals | |
| Calcium | 3.48 mg/g |
| Potassium | 62.1 mg/g |
| Magnesium | 6.3 mg/g |
| Manganese | 0.026 mg/g |
| Sodium | 10 mg/g |
| Phosphorous | 8.45 mg/g |
| Zinc | 0.033 mg/g |
| Heavy metals | |
| Arsenic | 5.6 ppm |
| Cadmium | 0.2 ppm |
| Lead | 1.7 ppm |
| Mercury | <0.01 ppm |

The blending of dried-milled Nori with the dried Nori extract in various ratios can be a means of ensuring consistent nutrient levels. The resulting composition can be organically certified as a nutritious sea vegetable source of vitamins, minerals, protein, and soluble fiber. The resulting composition can also be a good source of essential amino acids, antioxidant pigments, B vitamins, and minerals such as calcium, zinc and magnesium. Another attribute is its low sodium and high potassium contents. In addition, it can be low in fat, and the fat that is present is primarily the polyunsaturated omega-3 fatty acid eicosapentaenoic acid.

Example 2

Diabetes Cell Model

Figure 2:
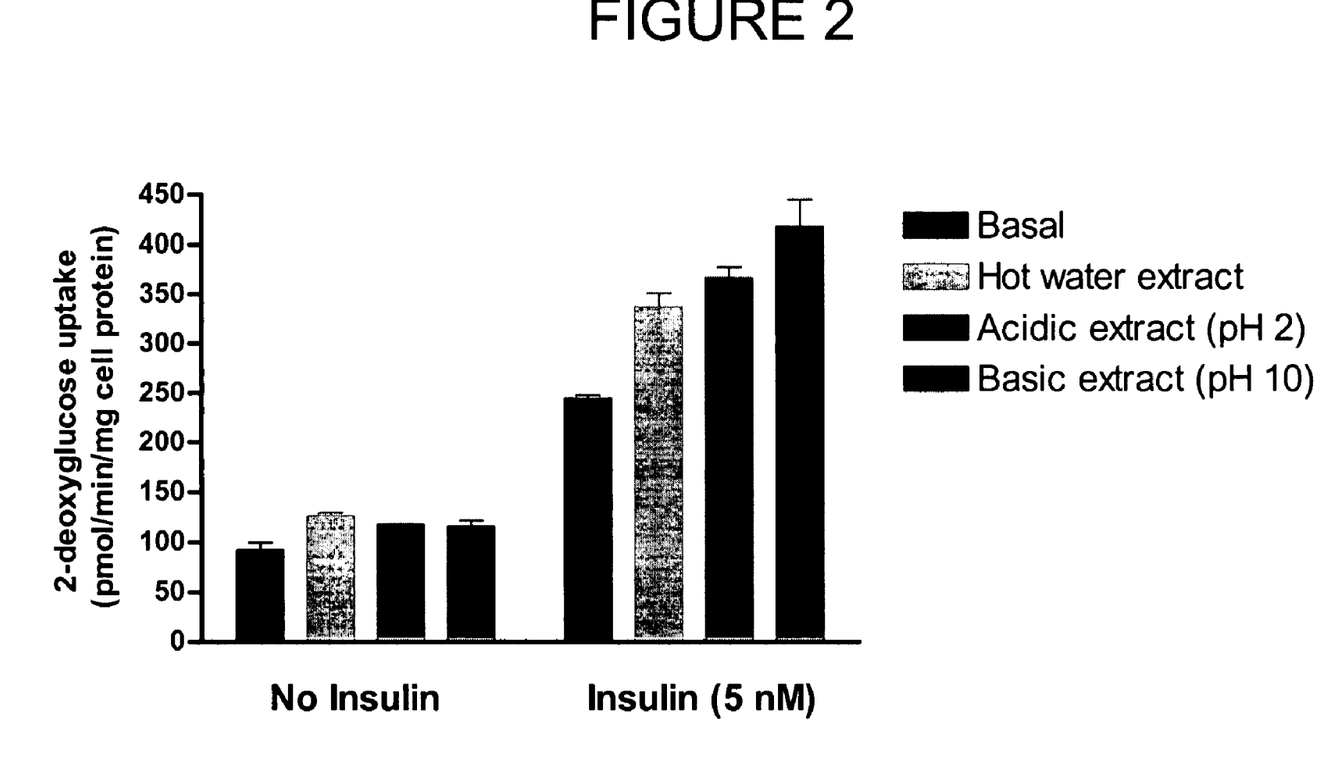
FIG. 2 is a histogram showing the stimulatory effect of Nori extract on glucose uptake by 3T3-L1 preadipocyte cells.

The 3T3-L1 cell line, obtained from the American Type Tissue Culture Collection (Manassas, Va.), is a well characterized model for studying insulin-mediated events of fat cells (see e.g., Pessin and Bell, "Mammalian facilitative glucose transporter family: structure and molecular regulation," *Annu. Rev. Physiol.*, 54:911-930, 1992). Upon differentiation, these cells share many biochemical and morphological characteristics of mature fat cells, including insulin-sensitive glucose uptake. Differentiated 3T3-L1 adipocytes were incubated at 37° C. for 20 minutes without insulin or with insulin (100 nM) and containing, or not, various concentrations of Nori extract and its fractions. The treatment was stopped by removal of media followed by a wash step with 1 mL of uptake buffer (PBS pH 7.4, 0.5 mM $MgCl_2$, 1 mM $CaCl_2$, 2.5 mM KCl). Cells were then incubated at 28° C. in uptake buffer containing 50 μM deoxy-glucose (50 μM) and [3H]-deoxy-glucose (1 μCi/mL). Non-transporter-mediated 2-deoxyglucose uptake was determined in parallel in the presence of cytochalasin B (75 μM) and subtracted from both basal and stimulated uptake measurements. The uptake was stopped after 10 minutes by aspiration of the uptake buffer solution and rapidly washing the wells twice with 1 mL ice-cold 0.9% NaCl. Cells were lysed in 0.05 M NaOH (1 mL/well) and 800 μL of the lysate was mixed with 3 mL of scintillation fluid and radioactivity was determined. The remaining lysate was saved for determination of cell protein content using the Coomassie protein assay with bovine serum albumin as standard. A representative experiment is shown in FIG. 2 where 300 μg/mL of Nori extract was used without and with (5 nM) insulin. These findings show that Nori extract contains a constituent(s) that stimulated the transport of glucose into fat cells.

The Nori extract used in this example was obtained by first extracting Nori powder from Noritech Seaweed Biotechnologies Ltd (Yokneam; Israel) with hexane. The remaining residue was next extracted with ethanol (95%). The residue from this extraction was then extracted with water at room temperature. Finally, the residue from the room-temperature-water extraction was extracted with water at 80° C. This final hot-water extract was the Nori extract used in this example.

Example 3

Type II Diabetes Mouse Model

Type II diabetes was produced in mice by low-dose injections of streptozotocin (35 mg/kg body weight dissolved in sodium citrate buffer, pH 4.5) daily for 5 days. Streptozotocin destroys insulin-producing β-cells of the pancreas. The protocol used C57BL/6J mice fed a diet high in fat and sucrose (No. D12451, Research Diets Inc., New Brunswick, N.J.). The combination of streptozotocin treatment and the high fat/high sucrose diet produce the type II diabetic condition. Glucose level was measured using a glucometer on a drop of blood obtained from saphenous vein. Mice were used for study if their blood glucose level was between 15 and 30 mM.

Mice were deprived of food for about 2 hours prior to the start of an experiment. An initial blood glucose level was determined (time 0) and then the Nori extract (Nori extract 217.4), dissolved in phosphate-buffered saline (PBS), was administered by intraperitoneal injection (100 mg per kg body weight) or by oral gavage (500 mg per kg body weight). Control animals receive PBS alone (controls). Blood glucose was measured at 1, 3, and 6 hours following administration. Results of these investigations are shown in FIGS. 3A and 3B.

The Nori extract (ON0217.4) used in this example was obtained by first extracting Nori powder from Noritech Seaweed Biotechnologies Ltd (Yokneam; Israel) with hexane. The remaining residue was next extracted with ethanol (95%). The residue from this extraction was then extracted with water at room temperature. Finally, the residue from the room-temperature-water extraction was extracted with water at 80° C. This final hot-water extract is identified herein as ON0217.4.

Figure 3:
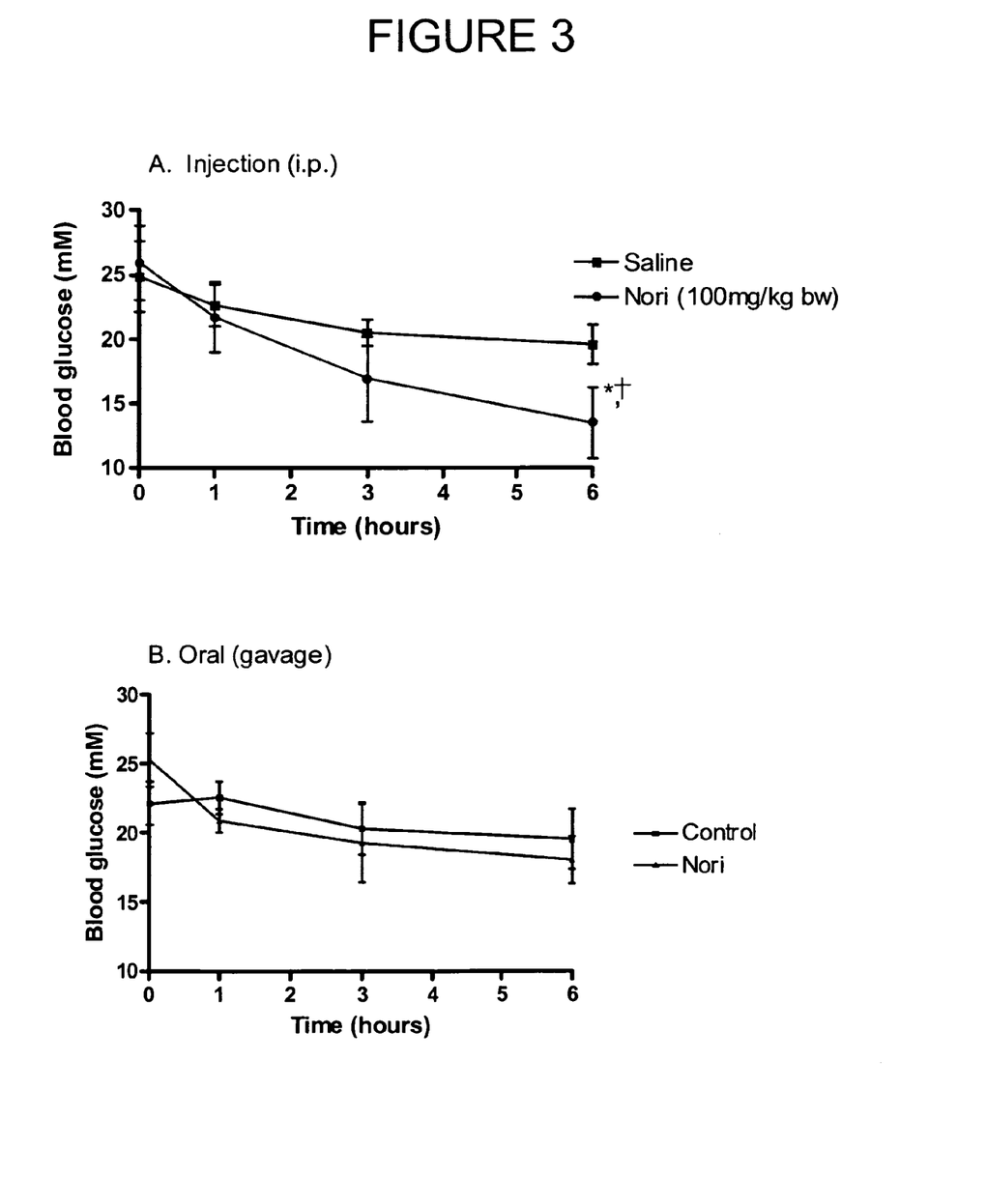
FIG. 3A is a graph of blood glucose levels (mM) in mice following i.p. injection of saline (control) or Nori extract (100 mg/kg body weight).
FIG. 3B is a graph of blood glucose levels (mM) in mice following administration of saline (control) or Nori extract (100 mg/kg body weight) via oral gavage.

This aqueous Nori extract was found to produce a significant reduction in blood glucose in diabetic mice when injected at a dose of 100 mg/kg body weight (FIG. 3A). The reduction was evident within 6 hours of treatment. Nori (500 mg/kg body weight), given as an oral gavage, did not produce a significant blood glucose reduction over a 6-hour period but there was a trend toward lowered blood glucose levels (FIG. 3B).

These studies were carried out in full compliance with regulations of the Canadian Council on Animal Care.

Example 4

Immunomodulatory Activity

RAW264.7 cells, a mouse macrophage cell line obtained from the American Tissue culture Collection (Rockville, Md.), were used for testing of Nori extracts for immunomodulatory activity. The production of nitric oxide was used as a marker of macrophage activation. The RAW 264.7 cells were seeded in 48-well plates at a density of $2.5 \times 10^5$ cells per well in culture medium (without phenol red) and grown overnight (80-90% confluency). Cells were then treated with 3.91, 7.91, 15, 31.25, and 62.5 µg/mL of Nori extract (ON201.4) or *Chlorella pyrenoidosa* extract (CPE; RESPONDIN™), or 5 µg/mL lipopolysaccharide (LPS). Control cells received culture medium alone. After 24 hours the culture medium was collected and frozen. Nitric oxide production was assessed by measuring nitrite level using Griess Reagent (1.0% sulfanilamide, 0.10% N-(1-naphthyl)-ethylenediamine dihydrochloride and 2.5% phosphoric acid). Fifty microliters of culture medium was mixed with 50 µL of Griess Reagent, incubated at room temperature for 10 minutes, and the resulting absorbance was measured at 550 nm. Sodium nitrite dissolved in deionized water was used as standard.

Figure 4:
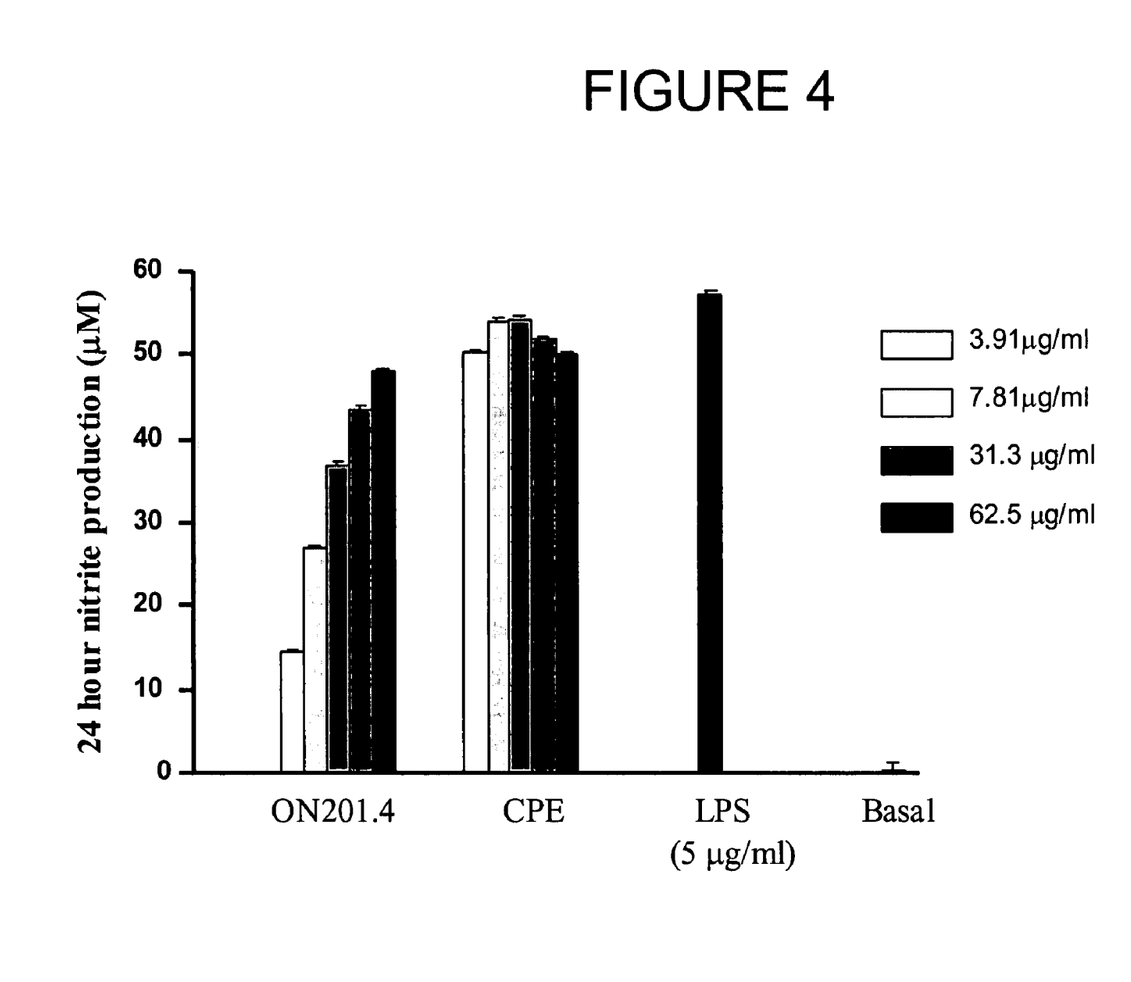
FIG. 4 is a histogram showing a comparison of nitric oxide production (μM) in RAW264.7 macrophage cells treated with Nori extract, *Chlorella pyrenoidosa* extract (CPE; RESPONDIN™ from Ocean Nutrition Canada, Dartmouth Canada), and lipopolysaccharide (LPS).

This test of Nori revealed that water from serial extractions as well as single step extractions resulted in a significant activation of macrophages. Dose-response studies showed that a water extract (ON0201.4) resulted in comparable nitrite generation to that produced by *Chlorella pyrenoidosa* extract (CPE; RESPONDIN™), a product known to have immunomodulatory activity (FIG. 4).

The Nori extract (ON0201.4) used in this example was obtained by first extracting Nori powder from Noritech Seaweed Biotechnologies Ltd (Yokneam; Israel) with hexane. The remaining residue was next extracted with ethanol (95%). The residue from this extraction was then extracted with water at room temperature. Finally, the residue from the room temperature water extraction was extracted with water at 80° C. This final hot water extract is identified herein as ON0201.4.

Example 5

Proliferation Response

Figure 5:
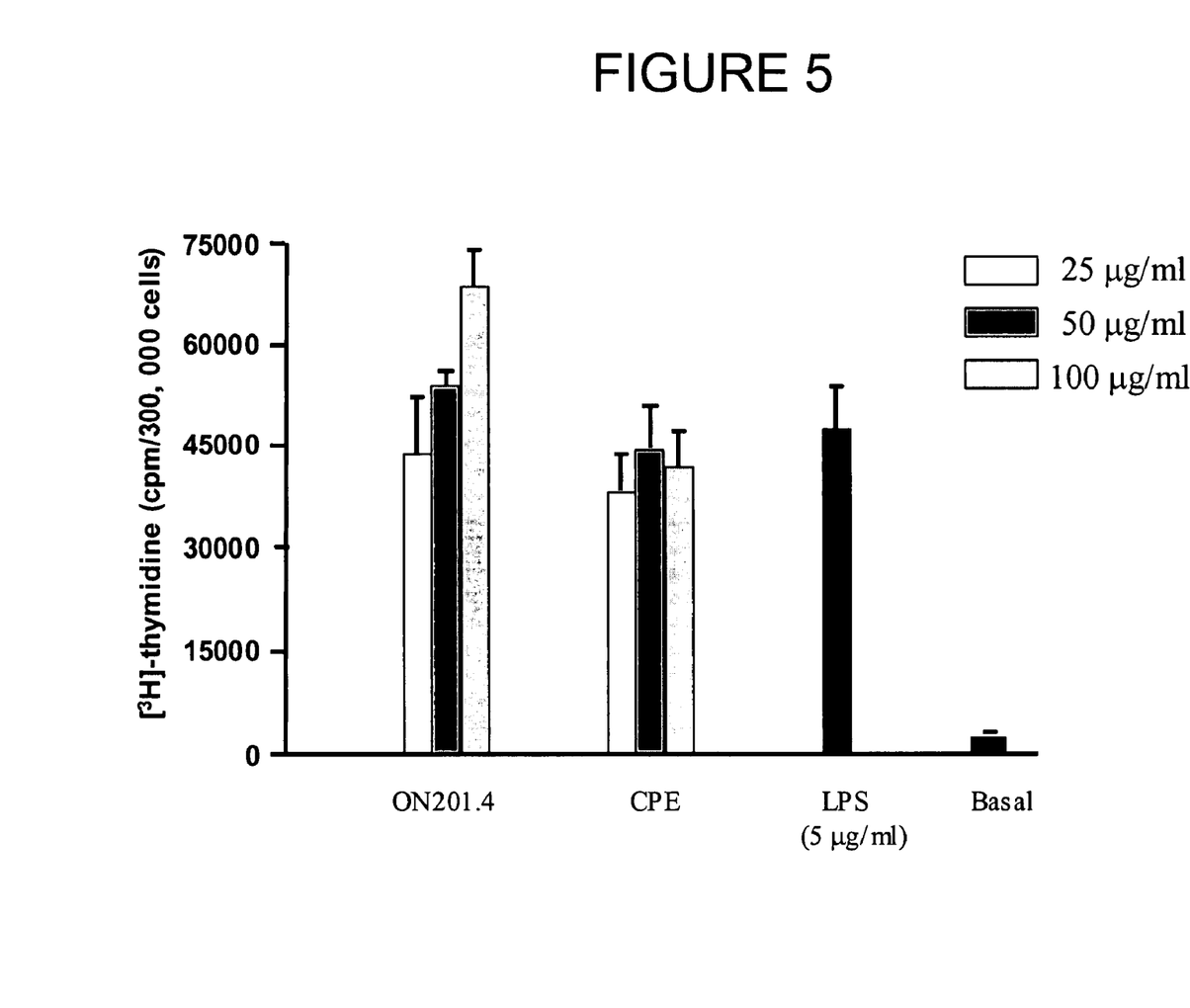
FIG. 5 is a histogram showing the effect of Nori extract, *Chlorella pyrenoidosa* extract (CPE; RESPONDIN™), and lipopolysaccharide (LPS) on mouse splenocyte proliferation.

Nori extract was tested for its ability to stimulated proliferation of mouse spleen cells. BALB/c mice between 9-16 weeks of age were killed by cervical dislocation, their spleens removed under aseptic conditions, and the splenocytes isolated. Splenocytes were plated at $3 \times 10^5$ cells/well in 0.1 mL of RPMI 1640 medium in 96-well flat bottom tissue culture plates. Nori extract (ON201.4) was dissolved in the cell medium and was added to triplicate wells to give a final volume of 0.2 mL/well. The plates were incubated at 37° C. under a humidified atmosphere of 95% $O_2$/5% $CO_2$. LPS (20 ng/mL) was added to triplicate wells as a positive control. After 48 hours, the cells were pulsed with [$^3$H]-thymidine (1 µCi/well in 10 µL RPMI) and incubated for an additional 18 hours. Cells were harvested onto glass fiber filters and the associated radioactivity determined by liquid scintillation counting. As shown in FIG. 5, Nori extract (ONO201.4) produced a dose-dependent proliferative response comparable to *Chlorella pyrenoidosa* extract (CPE; RESPONDIN™), a product known to have immunomodulatory activity.

Specific Embodiments

In certain aspects, disclosed herein are compositions comprising a blend of *Porphyra* and an extract of *Porphyra*. Also disclosed are compositions comprising an extract of *Porphyra*, wherein the extract is obtained by extracting a *Porphyra* powder with a first organic extraction solvent, thereby providing a first extracted residue; extracting the first extracted residue with a second organic extraction solvent, thereby providing a second extracted residue; and extracting the second extracted residue at least once with water, thereby providing the extract of *Porphyra*. Still further, disclosed are compositions comprising an extract of *Porphyra*, wherein the extract is obtained by providing a *Porphyra* powder by the steps comprising (i) growing spores and sporlings of *Porphyra* in a suspension culture; (ii) transferring matured sporlings to a cultivation tank; (iii) harvesting full-grown seaweed; and (iv) drying and grinding the harvested seaweed, thereby providing the *Porphyra* powder; extracting the *Porphyra* powder with hexane, thereby providing a first extracted residue; extracting the first extracted residue with ethanol, thereby providing a second extracted residue; extracting the second extracted residue with water at room temperatures, thereby providing a third extracted residue; and extracting the third extracted residue with water at from about 60 to 95° C., thereby providing the extract of *Porphyra*. Also disclosed are methods of preparing a nutritional composition by combining *Porphyra* with an extract of *Porphyra*. Also disclosed are compositions prepared by the disclosed methods. Tablets, capsules, or sachets comprising any of the disclosed compositions are also disclosed.

In the disclosed compositions and methods, the *Porphyra* can comprise *P. yezoensis*, *P.* sp. *Taiwanese*, or a mixture thereof. In the disclosed compositions, the *Porphyra* can comprise *P. abbotae*, *P. acanthophora*, *P. atropurpurae*, *P. columbina*, *P. crispata*, *P. fallax*, *P. leucostica*, *P. perforata*, *P. pseudolanceolata*, *P. spirilis*, *P. suborticulata*, *P. torta*, *P. umbilicalis*, *P. vietnamensis*, *P. tenera*, *P. haitanensis*, *P. pseudolinearis*, *P. kuniedae*, *P. arasaki*, *P. purpurea*, *P.*

*seriata*, or mixtures thereof. The extract of *Porphyra* can be a dried aqueous extract. The *Porphyra* can be dried-milled. The extract of *Porphyra* can be a dried extract. About 1:1 parts by weight of *Porphyra* to the extract of *Porphyra* can be used in the disclosed compositions and methods (i.e., about 1 part by weight of *Porphyra* can be combined with about 1 part by weight of the extract of *Porphyra*).

Further, the *Porphyra* can be washed before being ground and used in the disclosed compositions and methods. Also, the extract of *Porphyra* can be obtained by an aqueous extraction. The extract of *Porphyra* can be a combination of two or more aqueous extractions. The extract of *Porphyra* can be obtained by an organic extraction. The extract of *Porphyra* can be obtained by one or more organic extractions and one or more aqueous extractions.

In the disclosed compositions, the moisture content can be less than about 6%, the residue on ignition (Ash) can be less than about 40%, the total dietary fiber can be greater than about 25%, or the total lipids can be greater than about 0.5%, based on the total weigh of the composition. The disclosed compositions can comprise from about 7.0 to about 11.0 mg/g of phycoerythrin, from about 3.0 to about 6.0 mg/g of phycocyanin, from about 0.1 to about 0.5 mg/g of chlorophyll a, from about 0.001 to about 0.100 mg/g of lutein, or from about 0.010 to about 0.050 mg/g of beta-carotene. The disclosed compositions can have antioxidant activity of from about 40 to about 60 μmole TE/g. The total protein content of the composition can be from about 25 to about 50%, the total essential amino acid content can be from about 7.0 to about 10%, or the total conditionally essential or non-essential amino acid content can be from about 10 to about 30%, based on the total weight of the composition. The disclosed compositions can comprise at least about 6 mg/g isoleucine, at least about 14 mg/g leucine, at least about 10 mg/g lysine, at least about 2 mg/g methionine, at least about 6 mg/g phenylalanine, at least about 10 mg/g threonine, at least about 0.1 mg/g tryptophan, at least about 10 mg/g valine, at least about 25 mg/g alanine, at least about 20 mg/g arginine; at least about 15 mg/g aspartic acid, at least about 5 mg/g cystine, at least about 25 mg/g glutamic acid, at least about 12 mg/g glycine, at least about 1 mg/g histidine, at least about 7 mg/g proline, at least about 5 mg/g tyrosine, or at least about 9 mg/g taurine. The disclosed compositions can comprise at least about 0.1 mg/g vitamin C, at least about 15 μg/g B1 (Thiamin), at least about 35 μg/g B2 (Riboflavin), at least about 115 μg/g B3 (Niacin), at least about 9 μg/g B6 (Pyridoxine), or at least about 7 μg/g folic acid. The disclosed compositions can comprise at least about 1 mg/g calcium, at least about 50 mg/g potassium, at least about 4 mg/g magnesium, at least about 0.0075 mg/g manganese, at least about 6 mg/g sodium, at least about 6 mg/g phosphorous, or at least about 0.0075 mg/g zinc. The disclosed compositions can comprise less than about 7 ppm arsenic, less than about 0.75 ppm cadmium, less than about 3 ppm lead, or less than about 0.1 ppm mercury.

In the disclosed methods, the first organic extraction solvent can comprises hexane. In the disclosed methods, the second organic extraction solvent can comprises ethanol. In the disclosed methods, the second extracted residue can be extracted with water at room temperature, thereby providing a third extracted residue, and the third extracted residue can be extracted with water at from about 60 to about 95° C., thereby providing an extract of *Porphyra*.

Also, disclosed are nutritional supplements comprising any of the disclosed compositions, pharmaceutical formulations comprising any of the disclosed compositions and a pharmaceutical carrier, and foodstuffs comprising any of the disclosed compositions. The disclosed foodstuffs can comprise a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar, a sauce, a gravy, a syrup, a nutritional bar, a beverage, a dry beverage powder, a jam, a jelly, a fish product, or companion pet food.

Moreover, disclosed are methods of supplementing nutrients in a subject that can comprise administering an effective amount of any of the compositions, nutritional supplements, pharmaceutical formulations, foodstuffs, tablets, capsules, or sachets disclosed herein to the subject. Disclosed are also methods of treating Type II diabetes, improving insulin sensitivity, and/or reducing hyperglycemia in a subject comprising administering an effective amount of any of the compositions, nutritional supplements, pharmaceutical formulations, foodstuffs, tablets, capsules, sachets disclosed herein to the subject.

Methods of modulating an immune response and/or spleen cell proliferation in a subject comprising administering an effective amount of any of the compositions, nutritional supplements, pharmaceutical formulations, foodstuffs, tablets, capsules, sachets disclosed herein to the subject are also disclosed.

Disclosed are methods of inhibiting viral infection and/or treating inflammation in a subject comprising administering an effective amount of any of the compositions, nutritional supplements, pharmaceutical formulations, foodstuffs, tablets, capsules, sachets disclosed herein to the subject.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising:
    a dried-milled preparation of *Porphyra*, whereby the *Porphyra* has not been previously extracted; and
    an aqueous extract of *Porphyra*, wherein the composition is prepared by blending the dried-milled preparation of *Porphyra* with the aqueous extract of *Porphyra*, and wherein the aqueous extract of *Porphyra* is obtained by a process comprising the steps of:
    a. extracting a *Porphyra* powder with a first organic extraction solvent comprising hexane, thereby providing a first extracted residue;
    b. extracting the first extracted residue with a second organic extraction solvent, thereby providing a second extracted residue; and
    c. extracting the second extracted residue at least once with water, thereby providing the aqueous extract of *Porphyra*.

2. The composition of claim 1, wherein the second organic extraction solvent comprises ethanol.

3. The composition of claim 1, wherein the second extracted residue is extracted with water at room temperature, thereby providing a third extracted residue, and wherein the third extracted residue is extracted with water at a temperature of from about 60 to about 95° C., thereby providing the aqueous extract of *Porphyra*.

4. The composition of claim 1, wherein the composition comprises about 1:1 parts by weight of the dried-milled preparation of *Porphyra* to the dried aqueous extract of *Porphyra*.

5. The composition of claim 1, wherein the dried-milled preparation of *Porphyra* comprises *P. yezoensis*, *P.* sp. *Taiwanese*, or a mixture thereof.

6. The composition of claim 1, wherein the *Porphyra* comprises *P. abbotae*, *P. acanthophora*, *P. atropurpurae*, *P. columbina*, *P. crispata*, *P. fallax*, *P. leucostica*, *P. perforata*, *P. pseudolanceolata*, *P. spirilis*, *P. suborticulata*, *P. torta*, *P. umbilicalis*, *P. vietnamensis*, *P. tenera*, *P. haitanensis*, *P. pseudolinearis*, *P. kuniedae*, *P. arasaki*, *P. purpurea*, *P. seriata*, or mixtures thereof.

7. The composition of claim 1, wherein the moisture content is less than about 6%, the residue on ignition (Ash) is less than about 40%, the total dietary fiber is greater than about 25%, or the total lipids are greater than about 0.5%, based on the total weight of the composition.

8. The composition of claim 1, wherein the composition comprises from about 7.0 to about 11.0 mg/g of phycoerythrin, from about 3.0 to about 6.0 mg/g of phycocyanin, from about 0.1 to about 0.5 mg/g of chlorophyll a, from about 0.001 to about 0.100 mg/g of lutein, or from about 0.010 to about 0.050 mg/g of beta-carotene.

9. The composition of claim 1, wherein the composition has antioxidant activity of from about 40 to about 60 μmole TE/g.

10. The composition of claim 1, wherein the total protein content of the composition is from about 25 to about 50%, the total essential amino acid content is from about 7.0 to about 10%, or the total conditionally essential or non-essential amino acid content is from about 10 to about 30%, based on the total weight of the composition.

11. The composition of claim 1, wherein the composition comprises at least about 6 mg/g isoleucine, at least about 14 mg/g leucine, at least about 10 mg/g lysine, at least about 2 mg/g methionine, at least about 6 mg/g phenylalanine, at least about 10 mg/g threonine, at least about 0.1 mg/g tryptophan, at least about 10 mg/g valine, at least about 25 mg/g alanine, at least about 20 mg/g arginine; at least about 15 mg/g aspartic acid, at least about 5 mg/g cystine, at least about 25 mg/g glutamic acid, at least about 12 mg/g glycine, at least about 1 mg/g histidine, at least about 7 mg/g proline, at least about 5 mg/g tyrosine, or at least about 9 mg/g taurine.

12. The composition of claim 1, wherein the composition comprises at least about 0.1 mg/g vitamin C, at least about 15 μg/g B1 (Thiamin), at least about 35 μg/g B2 (Riboflavin), at least about 115 μg/g B3 (Niacin), at least about 9 μg/g B6 (Pyridoxine), or at least about 7 μg/g folic acid.

13. The composition of claim 1, wherein the composition comprises at least about 1 mg/g calcium, at least about 50 mg/g potassium, at least about 4 mg/g magnesium, at least about 0.0075 mg/g manganese, at least about 6 mg/g sodium, at least about 6 mg/g phosphorous, or at least about 0.0075 mg/g zinc.

14. The composition of claim 1, wherein the composition comprises less than about 7 ppm arsenic, less than about 0.75 ppm cadmium, less than about 3 ppm lead, or less than about 0.1 ppm mercury.

15. A nutritional supplement comprising the composition of claim 1.

16. A pharmaceutical formulation comprising the composition of claim 1 and a pharmaceutical carrier.

17. A foodstuff comprising the composition of claim 1.

18. The foodstuff of claim 17, wherein the foodstuff comprises a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar, a sauce, a gravy, a syrup, a nutritional bar, a beverage, a dry beverage powder, a jam, a jelly, a fish product, or companion pet food.

19. A tablet, capsule, or sachet comprising the composition of claim 1.

20. A method of supplementing nutrients in a subject, comprising administering an effective amount of a composition of claim 1 to the subject.

21. A method of treating Type II diabetes in a subject, comprising administering an effective amount of a composition of claim 1 to the subject.

22. A method of improving insulin sensitivity in a subject, comprising administering an effective amount of a composition of claim 1 to the subject.

23. A method of reducing hyperglycemia in a subject, comprising administering an effective amount of a composition of claim 1 to the subject.

24. A method of modulating spleen cell proliferation in a subject, comprising administering an effective amount of a composition of claim 1 to the subject.

25. A composition comprising:
a dried-milled preparation of *Porphyra*, whereby the *Porphyra* has not been previously extracted; and
an aqueous extract of *Porphyra* wherein the composition is prepared by blending the dried-milled preparation of *Porphyra* with the aqueous extract of *Porphyra*, and wherein the aqueous extract of *Porphyra* is obtained by a process comprising the steps of:
a. providing a *Porphyra* powder by the steps comprising:
   i. growing spores and sporlings of *Porphyra* in a suspension culture;
   ii. transferring matured sporlings to a cultivation tank;
   in. harvesting full-grown seaweed; and
   iv. drying and grinding the harvested seaweed, thereby providing the *Porphyra* powder;
b. extracting the *Porphyra* powder with hexane, thereby providing a first extracted residue;
c. extracting the first extracted residue with ethanol, thereby providing a second extracted residue;
d. extracting the second extracted residue with water at room temperature, thereby providing a third extracted residue; and
e. extracting the third extracted residue with water at a temperature of from about 60 to 95° C., thereby providing the aqueous extract of *Porphyra*.

* * * * *